United States Patent
Georgeson et al.

(10) Patent No.: US 9,989,483 B2
(45) Date of Patent: Jun. 5, 2018

(54) SYSTEMS AND METHODS FOR PERFORMING BACKSCATTER THREE DIMENSIONAL IMAGING FROM ONE SIDE OF A STRUCTURE

(71) Applicant: THE BOEING COMPANY, Huntington Beach, CA (US)

(72) Inventors: Gary E. Georgeson, Tacoma, WA (US); Morteza Safai, Newcastle, WA (US)

(73) Assignee: The Boeing Company, Chicago, IL (US)

( * ) Notice: Subject to any disclaimer, the term of this patent is extended or adjusted under 35 U.S.C. 154(b) by 94 days.

(21) Appl. No.: 14/827,653

(22) Filed: Aug. 17, 2015

(65) Prior Publication Data

US 2017/0052125 A1    Feb. 23, 2017

(51) Int. Cl.
G01N 23/20 (2018.01)
G01N 23/203 (2006.01)
G21K 1/02 (2006.01)
G21K 1/04 (2006.01)

(52) U.S. Cl.
CPC ..... *G01N 23/203* (2013.01); *G01N 23/20025* (2013.01); *G21K 1/043* (2013.01); *G01N 2223/1016* (2013.01); *G01N 2223/301* (2013.01)

(58) Field of Classification Search
CPC .............................. G01N 23/203; G21K 1/043
See application file for complete search history.

(56) References Cited

U.S. PATENT DOCUMENTS

| | | | |
|---|---|---|---|
| 5,181,234 A | 1/1993 | Smith | |
| 6,249,567 B1 * | 6/2001 | Rothschild | G01N 23/20 378/63 |
| 6,324,249 B1 * | 11/2001 | Fazzio | G01N 23/04 378/22 |
| 6,819,739 B2 * | 11/2004 | Eppler | G01N 23/04 378/207 |
| 7,400,701 B1 * | 7/2008 | Cason | G01V 5/0025 378/57 |
| 7,551,715 B2 * | 6/2009 | Rothschild | G01N 23/04 378/198 |
| 8,094,782 B1 * | 1/2012 | Annis | A61B 6/0435 378/37 |

(Continued)

*Primary Examiner* — David J Makiya
*Assistant Examiner* — Soorena Kefayati
(74) *Attorney, Agent, or Firm* — Armstrong Teasdale LLP (57) ABSTRACT

An imaging system for generating three dimensional image data using X-ray backscattering from one side of a structure is provided. The imaging system includes at least one X-ray source, at least one rotating collimator coupled to the at least one X-ray source, an X-ray detector, and a controller coupled to the at least one X-ray source, the at least one rotating collimator and the X-ray detector. The controller is configured to emit X-rays from the at least one X-ray source through the at least one rotating collimator towards the one side of the structure. Additionally, the controller is configured to detect backscattered X-rays from the one side of the structure, using the X-ray detector, at a plurality of depths within the structure. Additionally, the controller is configured to generate three dimensional image data of the structure based on the detected backscattered X-rays.

14 Claims, 11 Drawing Sheets

(56) References Cited

U.S. PATENT DOCUMENTS

| | | | | |
|---|---|---|---|---|
| 8,300,763 B2* | 10/2012 | Shedlock | ............ | G01N 23/046 |
| | | | | 378/57 |
| 8,582,720 B2* | 11/2013 | Morton | ................ | G01V 5/0008 |
| | | | | 378/57 |
| 8,594,272 B2* | 11/2013 | Funk | ...................... | A61B 6/032 |
| | | | | 378/10 |
| 8,680,475 B2 | 3/2014 | Konkle | | |
| 8,761,338 B2 | 6/2014 | Safai | | |
| 8,848,871 B2* | 9/2014 | Chapman | ............ | G01N 23/203 |
| | | | | 378/87 |
| 9,099,276 B1* | 8/2015 | Muray | ................... | H01J 37/04 |
| 9,103,769 B2* | 8/2015 | Duden | ................ | G01N 23/203 |
| 9,442,083 B2* | 9/2016 | Turner | ................ | G01N 23/203 |
| 2004/0066889 A1* | 4/2004 | Swift | ..................... | G01N 23/04 |
| | | | | 378/57 |
| 2010/0166285 A1* | 7/2010 | Schlomka | ............ | G01T 1/1644 |
| | | | | 382/132 |
| 2012/0321046 A1* | 12/2012 | Safai | .................... | G01N 23/203 |
| | | | | 378/86 |
| 2013/0195248 A1 | 8/2013 | Rothschild et al. | | |
| 2013/0315368 A1* | 11/2013 | Turner | ................ | G01N 23/203 |
| | | | | 378/41 |
| 2015/0302594 A1* | 10/2015 | Moore | ................ | G06T 7/0057 |
| | | | | 348/47 |
| 2016/0209339 A1* | 7/2016 | Safai | .................... | G01N 23/203 |
| 2016/0334535 A1* | 11/2016 | Dreiseitel | ............. | G01V 5/005 |

\* cited by examiner

SYSTEMS AND METHODS FOR PERFORMING BACKSCATTER THREE DIMENSIONAL IMAGING FROM ONE SIDE OF A STRUCTURE

BACKGROUND

The present disclosure relates generally to X-ray backscatter imaging systems, and more particularly to generating three dimensional image data of features within a composite structure.

Known ultrasound systems do not provide information about the thickness of features, such as wrinkles, within a composite structure because they cannot "see" past the feature from one side. There is a need to supplement ultrasonic detection of wrinkles with a method that can quantify wrinkle thickness and better determine the shape of the wrinkles. Addressing this need would provide more accurate structural performance models and predictions. X-ray laminography provides sequential layers of information for the interior of a structure. However, existing X-ray laminography systems require access to both sides of a structure, in order to operate. X-ray backscatter systems provide a tool for seeing into structures from one side only. However, images collected for inspection or evaluation are typically two dimensional representations of a superposition of depth information. Various methods to collect three dimensional information have been attempted, but they have been impractical or slow with relatively poor accuracy, because of single X-ray insertion and collection angles.

X-ray computed tomography can obtain accurate three dimensional X-ray attenuation data, but requires access to all sides of the structure being analyzed. Accordingly, computed tomography cannot be used for inspecting large aircraft parts, such as a wing or fuselage. A portable system is needed that combines the best of the above methods: a one-sided inspection system for three dimensional imaging of hidden features within a composite structure.

BRIEF DESCRIPTION

In one aspect, an imaging system for generating three dimensional image data using X-ray backscattering from one side of a structure is provided. The imaging system includes at least one X-ray source, at least one rotating collimator coupled to the at least one X-ray source, an X-ray detector, and a controller coupled to the at least one rotating collimator and the X-ray detector. The controller is configured to emit X-rays from the at least one X-ray source through the at least one rotating collimator towards the one side of the structure. Additionally, the controller is configured to detect backscattered X-rays from the one side of the structure, using the X-ray detector, at a plurality of depths within the structure. Additionally, the controller is configured to generate three dimensional image data of the structure based on the detected backscattered X-rays.

In another aspect, a method for generating three dimensional image data using X-ray backscattering from one side of a structure is provided. The method includes emitting X-rays from at least one X-ray source through at least one rotating collimator towards the one side of the structure. The method additionally includes detecting backscattered X-rays from the one side of the structure, using an X-ray detector, at a plurality of depths within the structure and generating three dimensional image data of the structure based on the detected backscattered X-rays.

DETAILED DESCRIPTION

Described herein are implementations of a rotating collimator X-ray backscatter system for creating 3-D images (single and dual) through a laminography-type reconstruction. The disclosed system is portable, and scanning can be performed using a robotic arm, a stages system vacuum-mounted to a structure, a rotating stage mounted on the structure, or a crawling robot. Scanning is performed in a plane perpendicular to the structure, with each scatter point in space receiving a rotating pencil beam from two angles. These crossing beams can be made from two aligned rotating collimators (using shuttered or alternating beams), or a single rotating collimator that is precisely re-oriented (180 degrees) to scan a beam from the other side of the centerline, but in the same scan plane.

Combining of backscatter images from the two angles facilitates maximizing the scatter information from that location, and facilitates minimizing the scatter information from the surrounding area, similar to laminography. Collecting and combining measurements at each point (based on the equations defined herein), can produce a scatter intensity line, which can be combined with parallel adjacent lines to create image layers ("slices"). These layers can be created from the same depth (d) data, collected through incremental rotation or translation of the system relative to the structure, from data collected in the plane of the pencil beam scans, or from the planes perpendicular to both. A method of linear reconstruction with the dual sources, as described herein, enables a crawling robot or scanner mounted on a track to continuously collect data on extended paths autonomously. The layers of scatter intensity data described above can be analyzed individually or stacked to create 3-D scatter intensity data sets that can be analyzed and viewed using 3-D imaging software. Accordingly, features such as wrinkles, fiber waviness, voids, and gaps can be identified and quantified in 3-D space for analysis, structural model performance predictions, and decision-making.

Elements that serve a similar, or at least substantially similar, purpose are labeled with like numbers in each of FIGS. 1-15, and these elements may not be discussed in detail herein with reference to each of FIGS. 1-15. Similarly, all elements may not be labeled in each of FIGS. 1-15, but reference numerals associated therewith may be utilized herein for consistency. Elements, components, and/or features that are discussed herein with reference to one or more of FIGS. 1-15 may be included in and/or utilized with any of FIGS. 1-15 without departing from the scope of the present disclosure.

Figure 1:
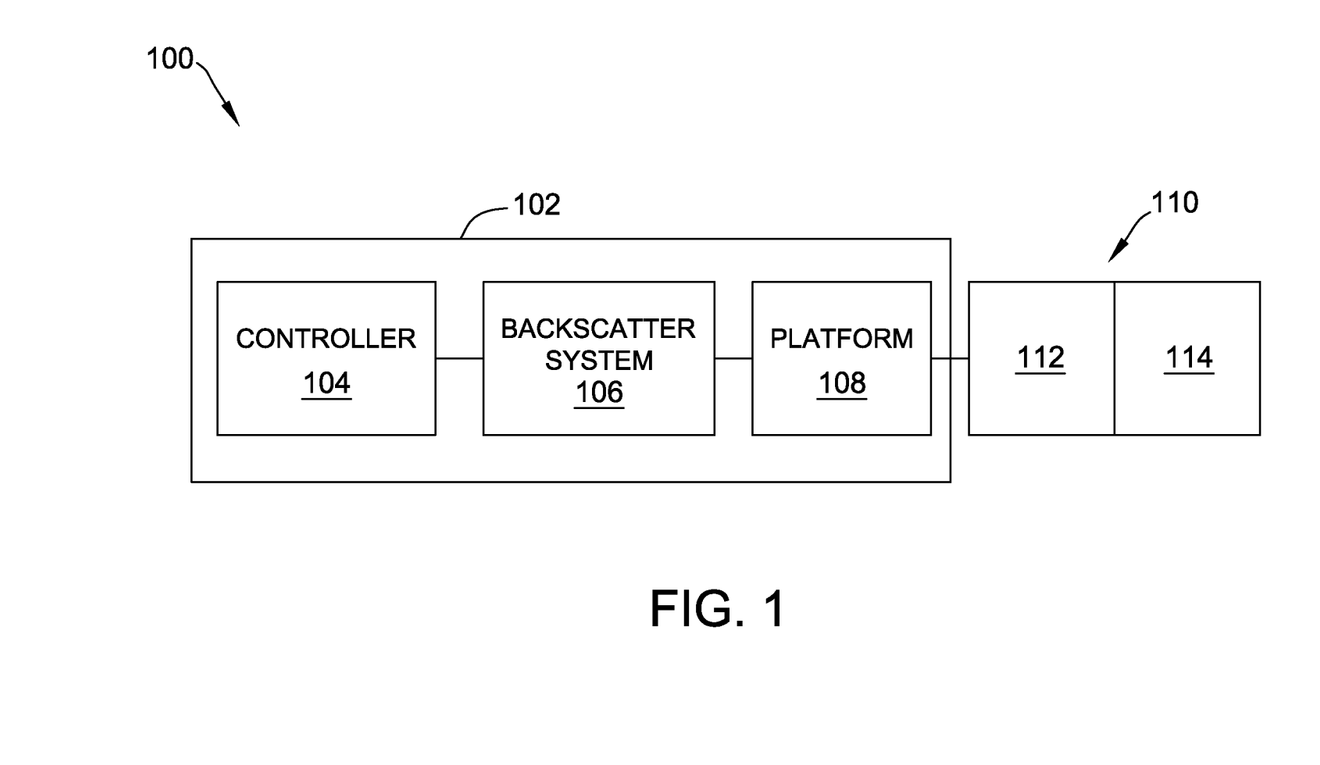
FIG. 1 is a diagram of an example environment including an imaging system and a structure that is imaged by the imaging system.

FIG. 1 is a diagram of an example environment 100 in which an imaging system 102 generates image data of a structure 110, for example a composite structure such as an aircraft wing or fuselage. Imaging system 102 includes a controller 104, for example a computing device that controls operations of a backscatter imaging system 106. Backscatter imaging system 106 includes one or more X-ray sources, one or more rotating collimators that collimate X-rays generated by one or more X-ray sources, and at least one detector, for example a scintillating detector, that receives backscattered X-rays from an object to be imaged (e.g., structure 110) and generates corresponding electrical signals representing intensities of the backscattered X-rays at each of a plurality of pixels. In at least some implementations, the one or more X-ray sources are stationary, and do not rotate with the respective collimator. In at least some implementations, backscatter system 106 is coupled to a platform 108, which moves imaging system 102 relative to structure 110. In some implementations, platform 108 is a robotic arm, a crawling robot, and/or one or more rotating or translating stages, which are components that rotate and/or translate about a structure to be analyzed (e.g., structure 110), as described in more detail herein. In some implementations, platform 108 can be mounted to structure 110, for example with vacuum mounts.

In some implementations, structure 110 is a portion of a vehicle, such as an aircraft. In operation, imaging system 102 is configured to emit X-rays into structure 110 at one or more depths and receive backscattered X-rays that provide information about features within structure 110 at each depth. For any given point at a given depth within structure 110, imaging system 102 emits separate X-ray beams at the point from two different angles and receives backscattered X-rays from each respective X-ray beam. Imaging system 102 generates imaging data from the backscattered X-rays from each respective X-ray beam and combines the imaging data to form three dimensional imaging data. Importantly, while structure 110 includes a first side 112 (e.g., a front side) and a second side 114 (e.g., back side), imaging system 102 only requires access to one of the sides (e.g., first side 112) to generate three dimensional imaging data of the inside of structure 110. Accordingly, imaging system 102 provides a convenient way to perform laminography of structure 110, without removing structure 110 from its current environment.

Figure 2:
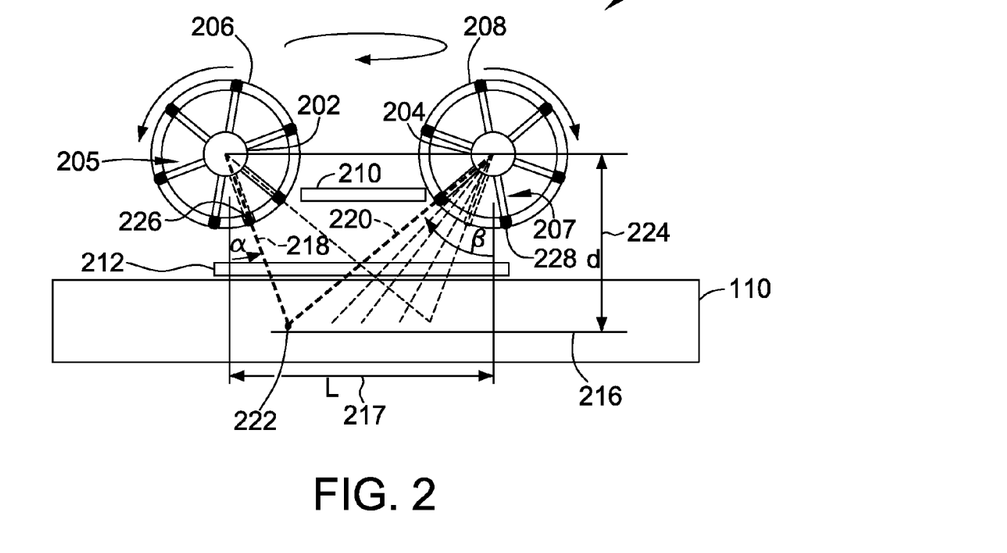
FIG. 2 is an elevation view of a first implementation of the imaging system.

FIG. 2 is an elevation view of a first example imaging system 200. More specifically, imaging system 200 is an implementation of imaging system 102. Imaging system 200 includes a first X-ray source 202 and a second X-ray source 204. First X-ray source 202 is coupled to a first rotating collimator 206 having a first plurality of apertures 205. First rotating collimator 206 has N (e.g., six) apertures 205, wherein each of the apertures are approximately equidistantly spaced around a center point or extend from a center point radially outward. By including multiple apertures in first rotating collimator 206, rather than just one aperture, imaging system 200 is able to collect data much more quickly. As the first collimator 206 rotates, for example in a counter-clockwise direction, one of the first plurality of apertures 205 directs a collimated pencil beam 218 towards structure 110. More specifically, first X-ray source 202 emits a fan beam, which is then collimated by first collimator 206. The output from first collimator 206 is collimated pencil beam 218. Likewise, second X-ray source 204 is coupled to a second rotating collimator 208 having a second plurality of apertures 207, arranged similarly to the apertures 205 of first collimator 206. As the second collimator 208 rotates, for example in a clockwise direction, one of the second plurality of apertures 207 directs a second collimated pencil beam 220 towards structure 110. Specifically, second X-ray source 204 emits a fan beam, which is then collimated into second collimated pencil beam 220 by second collimator 208. For a given point 222 along a line 216 within structure 110, imaging system 200 impinges point 222 with X-rays, generated by two different X-ray sources emitting X-rays from two different angles (e.g., first collimated pencil beam 218 and second collimated pencil beam 220). A detector 210 receives the backscattered X-rays (shown in FIG. 6) and generates corresponding electrical signals that are used by controller 104 (FIG. 1) to generate image data (shown in FIG. 4). As described in more detail herein, imaging system 200 includes shutters 226 and 228 that control the emission of X-rays from each collimator (e.g., first rotating collimator 206 and second rotating collimator 208) such that detector 210 receives backscattered X-rays from only one pencil beam at a time. In some implementations, imaging system 102 additionally or alternatively uses electronic shuttering of a power supply (e.g., alternatingly activating and deactivating the power supply) and/or synchronization of the rotating collimators 206 and 208 to avoid overlap of the pencil beams 218 and 220.

As stated above, every point (e.g., point 222) along line 216 has two angles of impingement, one angle of impingement (α) from the pencil X-ray beam 218 generated by the first X-ray source/collimator and a second angle of impingement (β) generated by the second X-ray source/collimator. Reconstruction of scatter intensities on a point by point basis is therefore associated with the angles of the X-rays impinging on the structure 110, as follows:

$$\tan(\alpha)+\tan(\beta)=L/d \qquad \text{(Equation 1)}$$

$$P_n=\tan(\alpha) \times d \qquad \text{(Equation 2)}$$

$$P_n=L-\tan(\beta) \times d \qquad \text{(Equation 3)}$$

When both α and β are at a zero angle, the ray is substantially perpendicular to the surface of the object being inspected (e.g., structure 110). Thus, the angle α or β is the angle defined between a ray that would be normal to the surface and the ray currently being emitted. Controller 104 combines image data collected at angle α, representing the angle the first pencil beam 218 impinges on the structure 110, and angle β, representing the angle of second pencil beam 220 emanating from second rotating collimator 208, to generate an image of an nth point ($P_n$) (e.g., point 222) along length L (e.g., length 217), representing a length of a line segment that backscatter imaging system 106 scans across, at a depth d (e.g., depth 224). Controller 104 causes backscatter imaging system 106 to scan (emit X-ray pencil beams and detect backscattered X-rays) at a plurality of positions (e.g., position 222) along lines (e.g., line 216) at different depths (e.g., depth 224) within structure 110. Furthermore, imaging system 200 includes a ring bearing 212, for example mounted to or incorporated into platform 108 (FIG. 1) that enables imaging system 200 to rotate relative to structure 110, as imaging system 200 scans structure 110.

Figure 3:
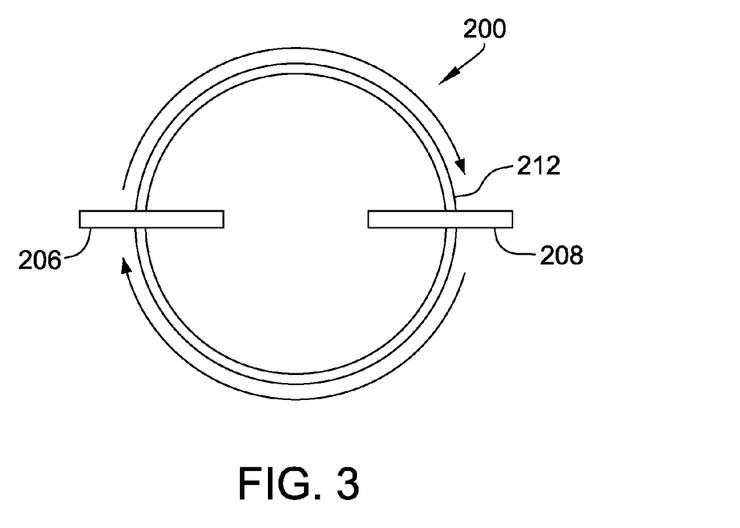
FIG. 3 is a top-down view showing rotation of the first implementation of the imaging system.

FIG. 3 is a top-down view showing rotation of imaging system 200. More specifically, the first rotating collimator 206 and the second rotating collimator 208 may be rotated 180 degrees on ring bearing 212 around a center point (e.g., a point halfway along length 217). Accordingly, for a given depth (e.g., depth 224), imaging system 200 generates a circular slice of image data. As described in more detail with reference to FIGS. 5 and 6, controller 104 combines the generated image data to generate three dimensional image data of structure 110.

Figure 4:
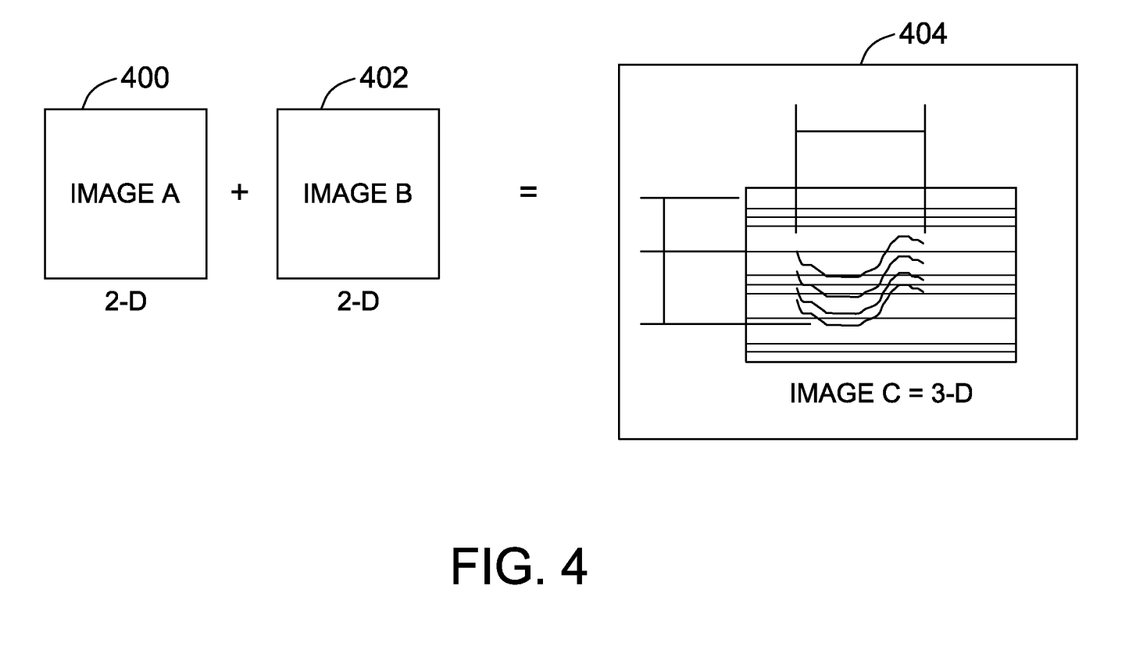
FIG. 4 is a diagram of first image data of the structure and second image data of the structure being combined into three dimensional image data.

FIG. 4 is a diagram of first image data 400 of structure 110 and second image data 402 of structure 110 being combined into three dimensional image data 404. More specifically, controller 104 receives, from detector 210, electrical signals for each pixel of detector 210. For example detector 210 transmits a voltage representing an intensity of backscattered X-rays for each respective pixel. Controller 104 generates first image data 400 based on intensities of X-rays backscattered from pencil beams (e.g. first pencil beam 218) emitted from first rotating collimator 206. Likewise, controller 104 generates second image data 402 based on intensities of X-rays backscattered from pencil beams (e.g. second pencil beam 220) directed out of second rotating collimator 208. Controller 104 then combines first image data 400 with second image data 402 to form three dimensional image data 404 (e.g., a stereoscopic image). For example, when viewed by a human, first image data 400 is displayed to a first eye and second image data 402 is displayed to a second eye to enable the viewer to perceive depth in three dimensional image data 404.

Figure 5:
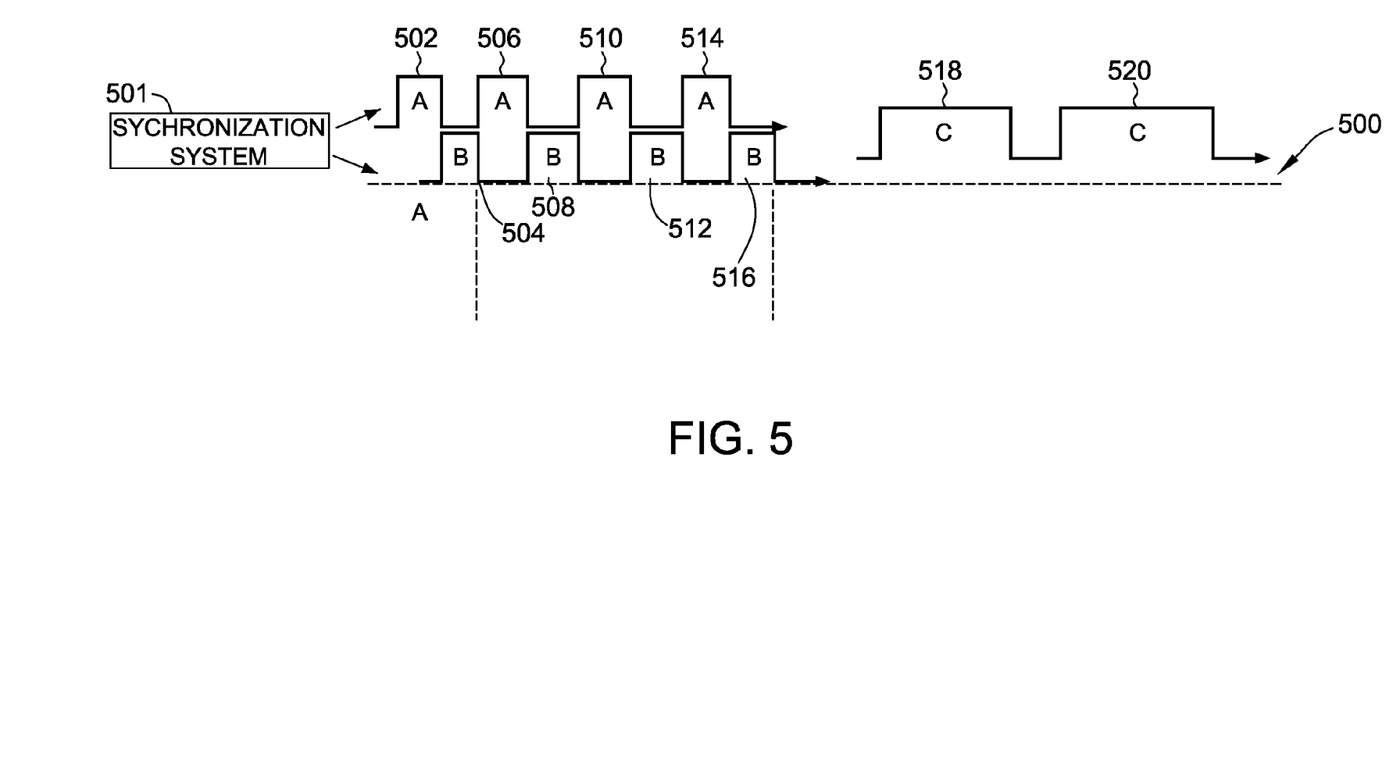
FIG. 5 is a timeline of synchronization of the first image data and the second image data to generate the three dimensional image data.

FIG. 5 illustrates a timeline 500 of synchronization of sets of first image data 400 and sets of second image data 402 to generate three dimensional image data 404. More specifically, a synchronization system 501, for example controller 104 in combination with shutters (e.g., shutters 226 and 228 shown in FIG. 6) coupled to first rotating collimator 206 and second rotating collimator 208, causes imaging system 200 to generate a first image datum 502 for a first point (e.g., point 222) from X-rays backscattered from first rotating collimator 206, then receive a second image datum 504 for the first point (e.g., point 222) from X-rays backscattered from second rotating collimator 208. Further, imaging system generates a third image datum 506 corresponding to a second different point along the same line from the first rotating collimator 206, a fourth image datum 508 of the second point from the second rotating collimator 208, etc. Thus, at each different point, two image datums are acquired, one from backscatter information acquired from backscatter associated with the first rotating collimator 206 and a second from the backscatter associated with the second rotating collimator 208. In the exemplary embodiment, images datums 502 . . . 516 are acquired. Imaging system 200 then combines corresponding data (e.g., first image datum 502 with second image datum 504, third image datum 506 with fourth image datum 508, etc.) to form stereoscopic image data (e.g., image data 518) along each scanned line at a given depth. Further, imaging system 200 combines the stereoscopic image data for each line at a given depth to produce a set of three dimensional image data 520 for a given plane or "slice" at the given depth. Further, the imaging system 200 may repeat the above process to generate parallel slices of image data 520, each slice corresponding to a different depth within structure 110.

Figure 6:
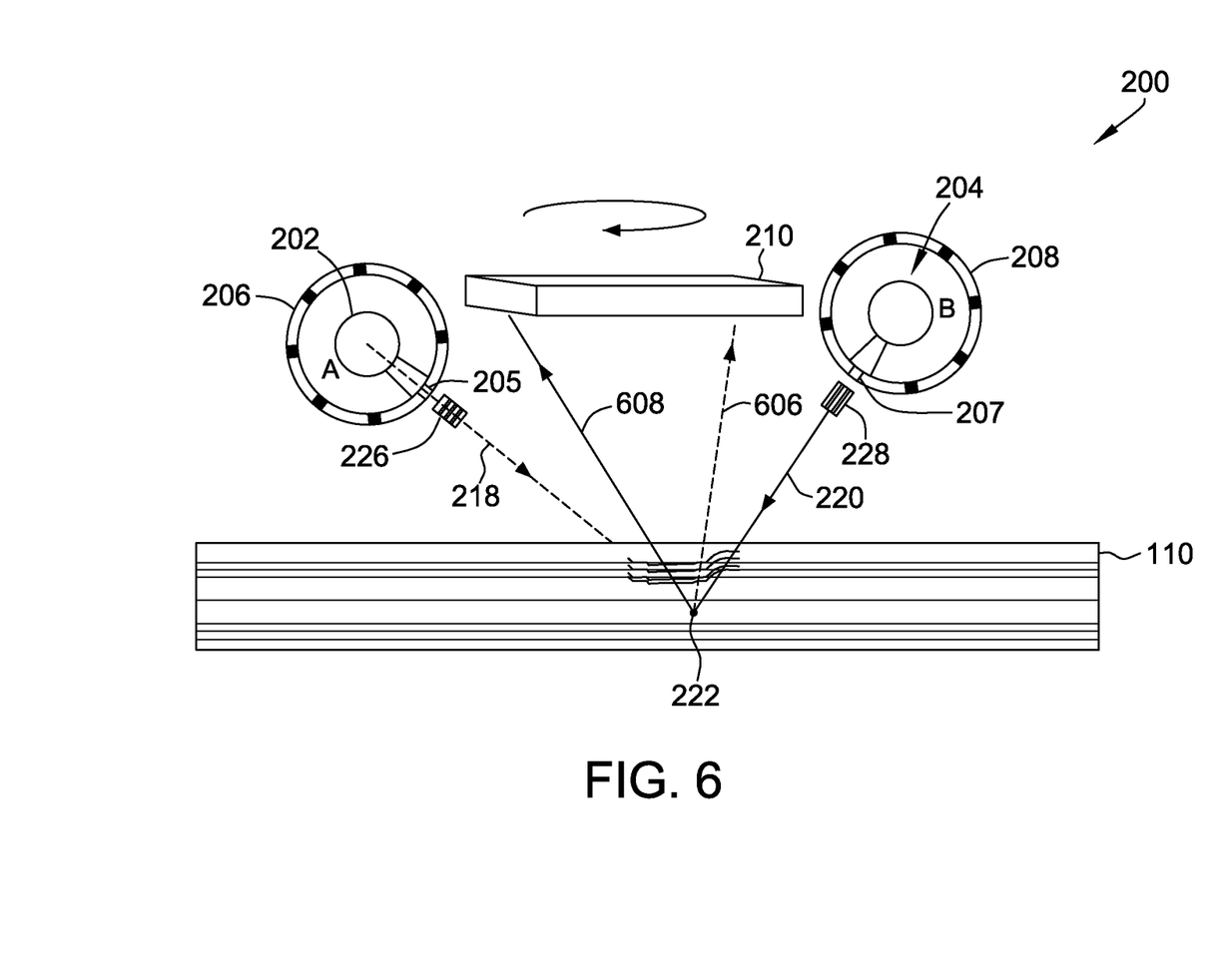
FIG. 6 is a diagram of backscattered X-rays being detected by the first implementation of the imaging system shown in FIG. 2.

FIG. 6 is a diagram of backscattered X-rays being detected by imaging system 200. A first shutter 226, for example a mechanical shutter, is coupled to aperture 205 of first rotating collimator 206. Likewise, a second shutter 228 is coupled to aperture 207 of second rotating collimator 208. In the exemplary embodiment, each aperture has its own shutter. More specifically, if the collimators 206 and 208 each have N apertures, the imaging system 200 will include N shutters, wherein each respective shutter is positioned in front of the aperture. First shutter 226 and second shutter 228 are synchronized, for example by electrical signals (not shown) from controller 104, such that first rotating collimator 206 outputs first pencil beam 218 while first shutter 226 is open and second shutter 228 is closed. Detector 210 then detects first backscattered X-rays 606 caused by first pencil beam 218 impinging on point 222 of structure 110. Subsequently, second rotating collimator 208 outputs second pencil beam 220 while first shutter 226 is closed and second shutter 228 is open. Detector 210 then detects second backscattered X-rays 608 caused by second pencil beam 220 impinging on the same point (e.g. point 222) of structure 110. Imaging system 200 continues operating in this manner, alternately emitting pencil beams from each X-ray source and detecting backscattered X-rays for each point along each line (e.g., line 216) within a plane or slice at each of a plurality of depths (e.g., depth 224) within structure 110.

Figure 7:
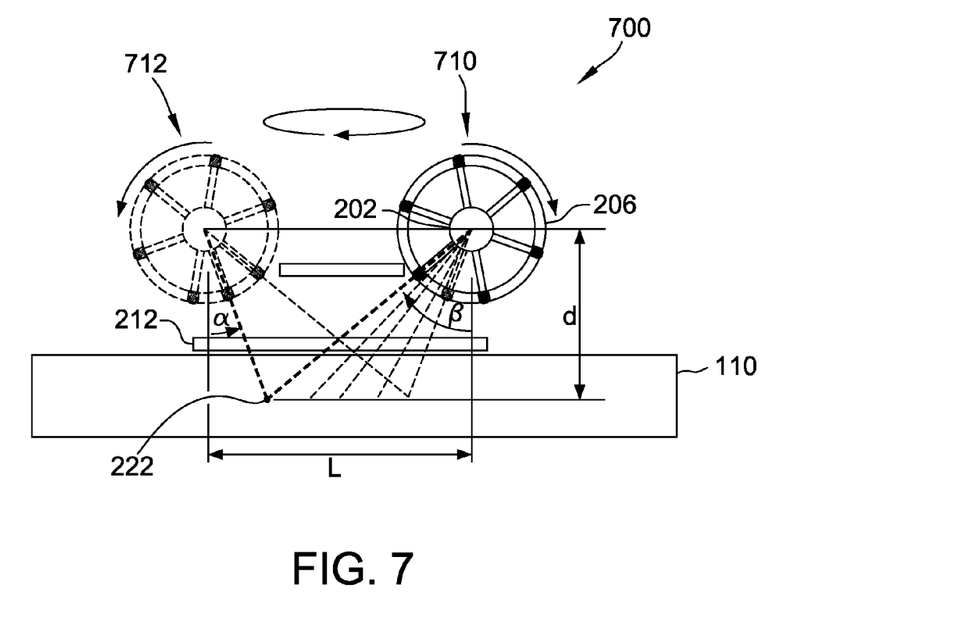
FIG. 7 is an elevation view of a second implementation of the imaging system.
Figure 8:
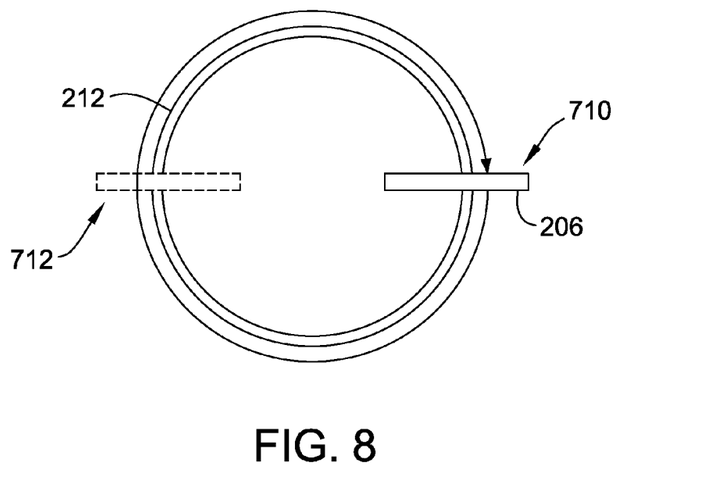
FIG. 8 is a top-down view showing rotation of the second implementation of the imaging system.

FIG. 7 is an elevation view of a second example imaging system 700. FIG. 8 is a top-down view showing rotation of imaging system 700. Imaging system 700 is an implementation of imaging system 102. Imaging system 700 is similar to imaging system 200 (shown in FIG. 3) except rather than having two X-ray sources and two rotating collimators, imaging system 700 includes only a single X-ray source 202 and a single rotating collimator 206. Imaging system 700 rotates 360 degrees on a ring bearing 212. Accordingly, rotating collimator 206 impinges point 222 with a pencil beam when rotating collimator 206 is at a first position 710, and when ring bearing has rotated 180 degrees from first position 710 such that rotating collimator 206 is at second position 712. Accordingly, Equations 1, 2, and 3, described with reference to imaging system 200 also apply to reconstruction of scatter intensities detected with imaging system 700. FIG. 8 is a top-down view showing rotation of imaging system 700.

Figure 9:
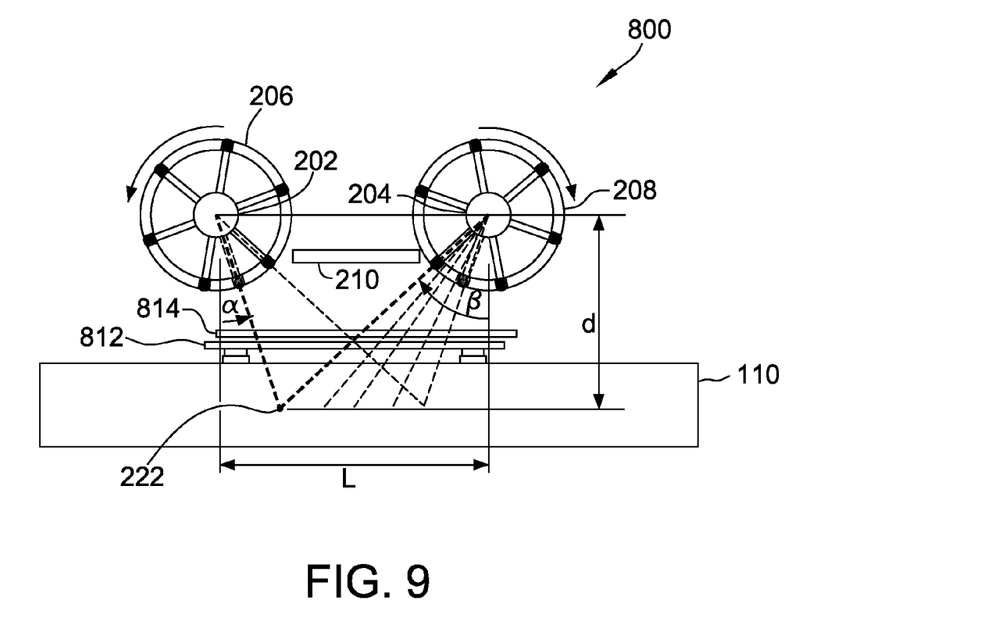
FIG. 9 is an elevation view of a third implementation of the imaging system.
Figure 10:
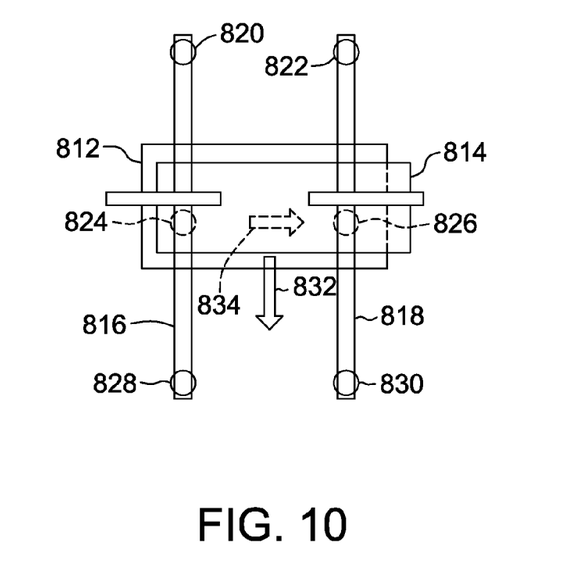
FIG. 10 is a top-down view showing stages that enable translation of the third implementation of the imaging system.

FIG. 9 is an elevation view of a third example imaging system 800. FIG. 10 is a top-down view of imaging system 800, showing stages that enable translation of imaging system along two axes. Imaging system 800 is an implementation of imaging system 102 and is similar to imaging system 200. Imaging system includes the first X-ray source 202, the second X-ray source 204, the first rotating collimator 206, the second rotating collimator 208, and the detector 210. Additionally, imaging system 800 includes shutters (not shown) coupled to first rotating collimator 206 and second rotating collimator 208, similar to first shutter 226 (FIG. 6) and second shutter 228 (FIG. 6), to synchronize the emission of pencil beams, as described above. However, unlike imaging system 200, platform 108 of imaging system 800 includes a first stage 812 that is coupled to a first rail 816 and a second rail 818.

First rail 816 and second rail 818 are coupled to a first vacuum mount 820, a second vacuum mount 822, a third vacuum mount 824, a fourth vacuum mount 826, a fifth vacuum mount 828, and a sixth vacuum mount 830. Vacuum mounts 820, 822, 824, 826, 828, and 830 attach to structure 110. First stage 812 includes a first stepper motor (not shown) that is configured to translate first stage 812 along a first axis 832 (e.g., an X-axis). In some implementations, platform 108 includes a second stage 814 that is coupled to first stage 812. Second stage 814 includes a second stepper motor (not shown) that is configured to translate second stage 814 along a second axis 834 (e.g., a Y-axis) that is perpendicular to first axis 832. Accordingly, in at least some implementations, controller 104 transmits electrical signals to first stage 812 and second stage 814 while imaging system 800 is scanning structure 110 to, for example, translate first stage 812 along rails 816 and 818 (i.e., first axis 832) while second stage 814 is at a first position along second axis 834, then translate second stage 814 to a second position along second axis 834, and then translate first stage 812 along rails 816 and 818 (i.e., first axis 832) while second stage 814 is at the second position along second axis 834. By including second stage 814, imaging system 800 is able to move incrementally between linear scans, such as across wrinkles or stiffener features, for additional scatter data around the feature, which can improve three dimensional imaging of the feature.

Figure 11:
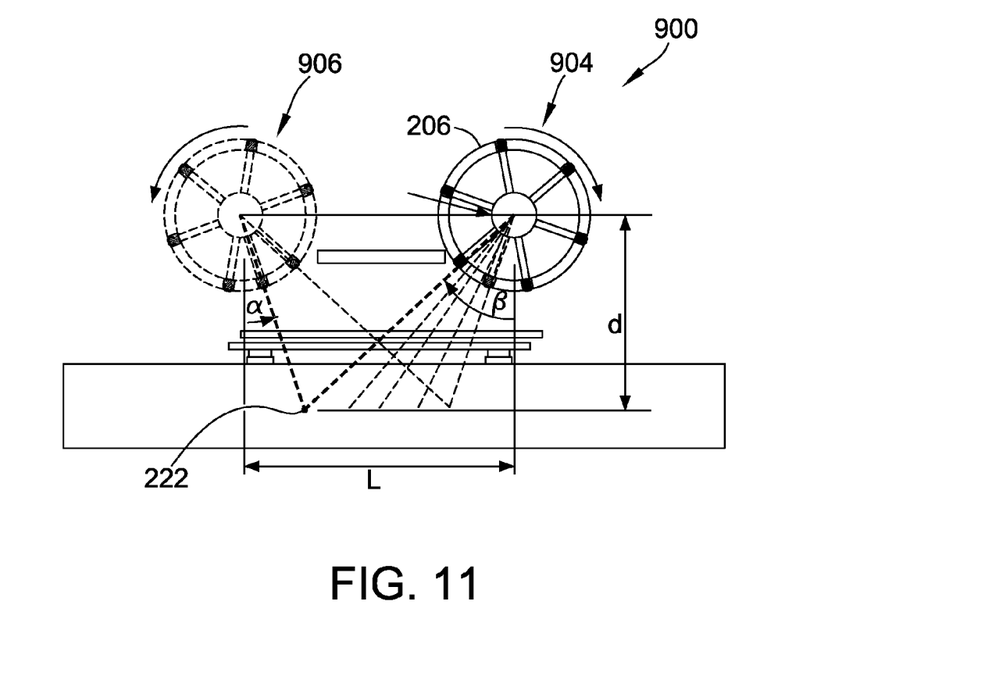
FIG. 11 is an elevation view of a fourth implementation of the imaging system.
Figure 12:
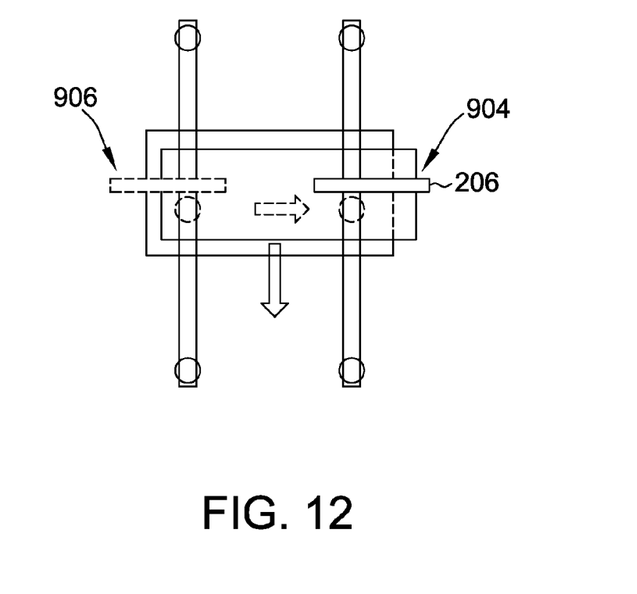
FIG. 12 is a top-down view of the fourth implementation of the imaging system.

FIG. 11 is an elevation view of a fourth example imaging system 900. FIG. 12 is a top-down view of imaging system 900. Imaging system 900 is an implementation of imaging system 102. Further, imaging system 900 is similar to imaging system 800, except instead of having two rotating collimators, imaging system 900 includes only one rotating collimator 206. Additionally, instead of synchronizing the emission of pencil beams from each collimator to impinge point 222 from two different angles, imaging system 900 scans structure 110 by impinging each point (e.g., point 222) with X-rays from when first collimator 206 is in a first position 904, then first collimator 206 is moved (e.g., remounted) to second position 906 and rescans structure 110. Accordingly, imaging system 900 takes twice as long as imaging system 800 to scan structure 110, but requires only a single rotating collimator (e.g., rotating collimator 206).

Figure 13:
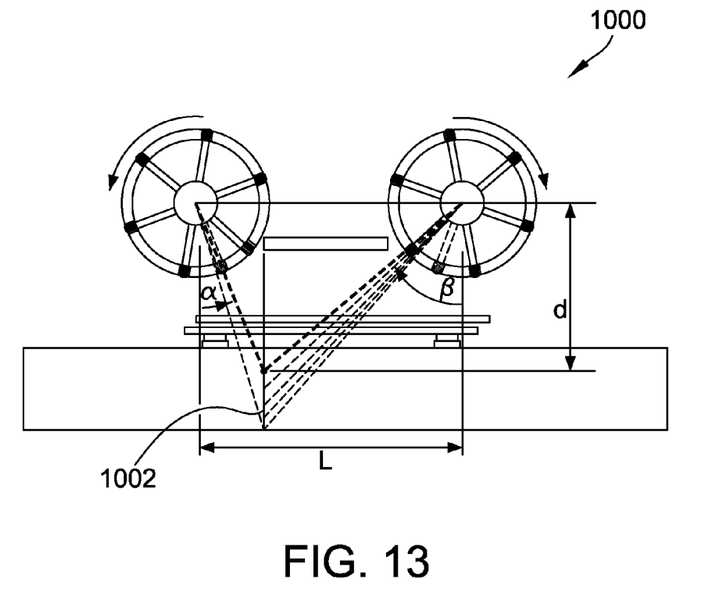
FIG. 13 is an elevation view of a fifth implementation of the imaging system.

FIG. 13 is an elevation view of a fifth example imaging system 1000. Imaging system 1000 is an implementation of imaging system 102 and is similar to imaging system 800, except as described herein. Rather than performing reconstruction of scatter intensities along a horizontal line (e.g., line 216 in FIG. 2), imaging system 1000 performs reconstruction along a vertical line 1002. Every point ($P_n$) along vertical line 1002 will have two angles of impingement (e.g., $\alpha$ and $\beta$) from pencil X-ray beams. More specifically, imaging system 1000 performs reconstruction according to the following equations:

$$\tan(\alpha) = P_n/d \quad \text{(Equation 4)}$$

$$\tan(\beta) = (L-P_n)/d \quad \text{(Equation 5)}$$

Imaging system 1000 combines images collected at $\alpha$ and $\beta$ during scanning, similar to the process described with reference to FIGS. 4 and 5 to generate three dimensional image data.

Figure 14:
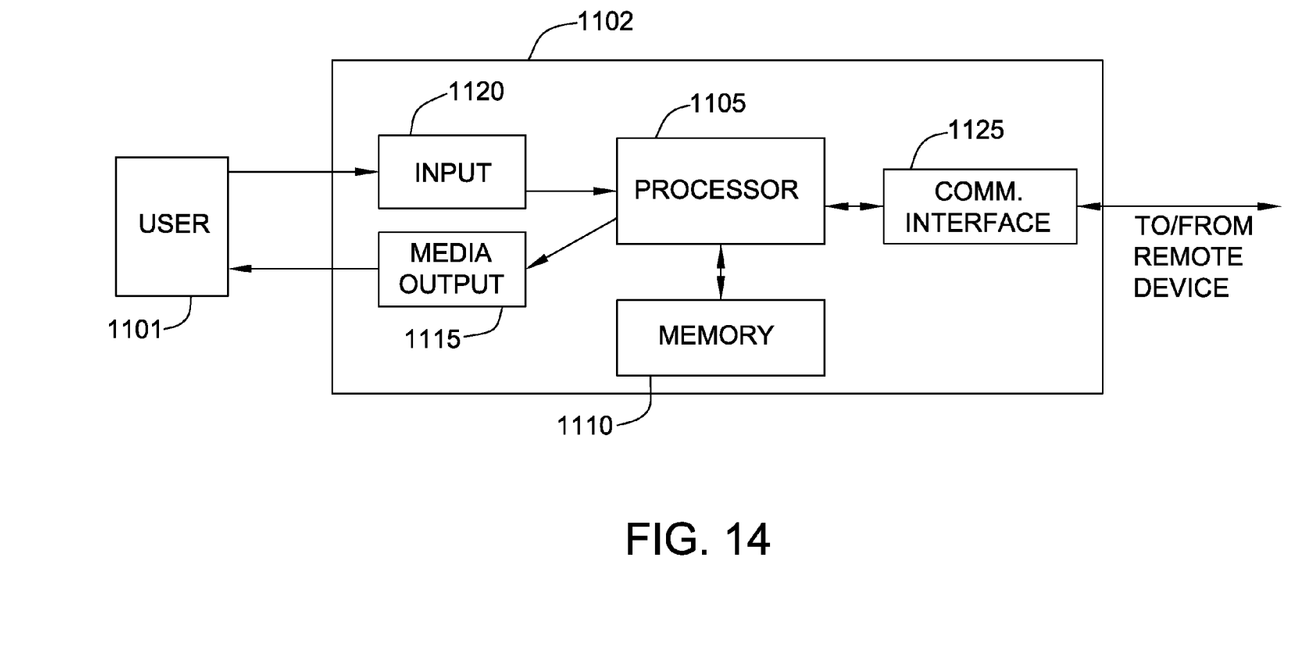
FIG. 14 is a diagram of an example computing device used in the environment of FIG. 1.

FIG. 14 is a diagram of an example computing device 1102. Computing device 1102 is representative of controller 104. Computing device 1102 includes one or more processors 1105 for executing instructions. In some implementations, executable instructions are stored in a memory device 1110. Processor 1105 may include one or more processing units (e.g., in a multi-core configuration). One or more memory devices 1110 are any one or more devices allowing information such as executable instructions and/or other data to be stored and retrieved. One or more memory devices 1110 may include one or more computer-readable media.

Computing device 1102 also includes at least one media output component 1115 for presenting information to a user 1101. Media output component 1115 is any component capable of conveying information to user 1101. In some implementations, media output component 1115 includes an output adapter such as a video adapter and/or an audio adapter. An output adapter is operatively coupled to processor 1105 and operatively couplable to an output device such as a display device (e.g., a liquid crystal display (LCD), organic light emitting diode (OLED) display, cathode ray tube (CRT), or "electronic ink" display) or an audio output device (e.g., a speaker or headphones).

In some implementations, computing device 1102 includes an input device 1120 for receiving input from user 1101. Input device 1120 may include, for example, a keyboard, a pointing device, a mouse, a stylus, a touch sensitive panel (e.g., a touch pad or a touch screen), a gyroscope, an accelerometer, a position detector, or an audio input device. A single component such as a touch screen may function as both an output device of media output component 1115 and input device 1120.

Computing device 1102 additionally includes a communication interface 1125, which is communicatively couplable to another device such as backscatter system 106 and/or platform 108. Communication interface 1125 may include, for example, a wired or wireless network adapter or a wireless data transceiver for use with a mobile phone network (e.g., Global System for Mobile communications (GSM), 3G, 4G or Bluetooth) or other mobile data network (e.g., Worldwide Interoperability for Microwave Access (WIMAX)).

Stored in one or more memory devices 1110 are, for example, computer-readable instructions for providing a user interface to user 1101 via media output component 1115 and, optionally, receiving and processing input from input device 1120. A user interface may include, text, graphics, and/or sound that enable user 1101 to interact with computing device 1102, for example to control operations of computing device 1102 and/or view output (e.g., three dimensional image data 404). The computer-readable instructions additionally cause computing device 1102 perform the processes for scanning structure 110, moving backscatter system 106, and combining image data into three dimensional image data.

Figure 15:
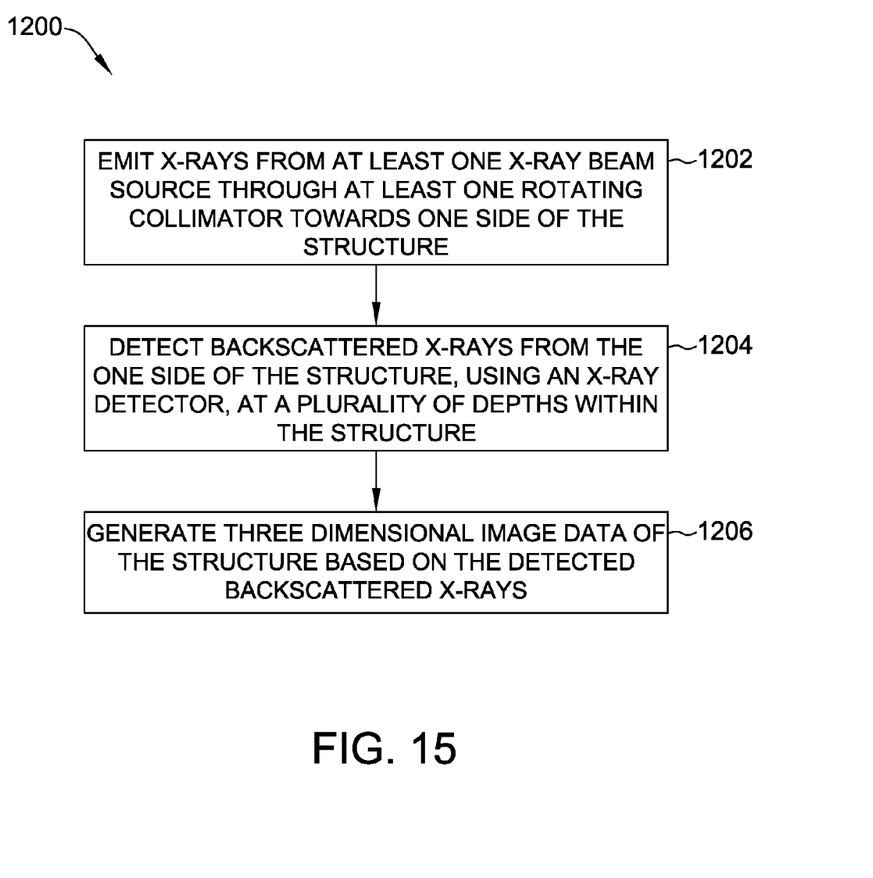
FIG. 15 is a flowchart of an example process for generating three dimensional image data using the imaging system shown in FIG. 1.

FIG. 15 is a flowchart of an example process 1200 for generating three dimensional image data using imaging system 102. Initially, imaging system 102 emits 1202 X-rays (e.g., first pencil beam 218 and second pencil beam 220) from at least one X-ray source (e.g., first X-ray source 202 and second X-ray source 204) through at least one rotating collimator (e.g., first rotating collimator 206 and second rotating collimator 208) towards one side (e.g., first side 112) of the structure 110. Additionally, imaging system 102 detects 1204 backscattered X-rays (e.g., first backscattered X-rays 606 and second backscattered X-rays 608) from the one side (e.g., first side 112) of the structure 110, using an X-ray detector (e.g., detector 210), at a plurality of depths (e.g., depths 224) within the structure 110. Further, imaging system 102 generates 1206 three dimensional image data (e.g., three dimensional image data 404) of the structure 110 based on the detected backscattered X-rays (e.g., first backscattered X-rays 606 and second backscattered X-rays 608).

In some implementations, imaging system 102 emits a first X-ray beam (e.g., first pencil beam 218) through the first rotating collimator (e.g., first rotating collimator 206) at a first point (e.g., point 222) in structure 110 while the second shutter (e.g., second shutter 228) is closed, detects backscattered X-rays (e.g., first backscattered X-rays 606) from the first X-ray beam (e.g., first pencil beam 218), emits a second X-ray beam (e.g., second pencil beam 220) through the second rotating collimator (e.g., second rotating collimator 208) at the first point (e.g., point 222) while the first shutter (e.g., first shutter 226) is closed, and detects backscattered X-rays (e.g., second backscattered X-rays 608) from the second X-ray beam (e.g., second pencil beam 220).

In some implementations, imaging system 102 emits a first X-ray beam (e.g., first pencil beam 218) at a first point (e.g., point 222) in the structure (e.g., structure 110) from a first angle (e.g., α), detects first backscattered X-rays (e.g., first backscattered X-rays 608) from the first X-ray beam (e.g., first pencil beam 218), generates first image data (e.g., first image data 400) from the first backscattered X-rays (e.g., first backscattered X-rays 608), emits a second X-ray beam (e.g., second pencil beam 220) at the first point (e.g., point 222) in the structure (e.g., structure 110) from a second angle (e.g., β), detects second backscattered X-rays (e.g., second backscattered X-rays 608) from the second X-ray beam (e.g., second pencil beam 220), generates second image data (e.g., second image data 402) from the second backscattered X-rays (e.g., second backscattered X-rays 608), and combines the first image data (e.g., first image data 400) with the second image data (e.g., second image data 402).

In some implementations, imaging system 102 includes a platform (e.g., platform 108) that is coupled to the structure (e.g., structure 110) and imaging system 102 is configured to translate across at least a portion (e.g., first side 112) of the structure (e.g., structure 110) while emitting the X-rays (e.g., first pencil beam 218 and second pencil beam 220) and detecting the backscattered X-rays (e.g., first backscattered X-rays 606 and second backscattered X-rays 608).

In some implementations, imaging system 102 includes a platform (e.g., platform 108) that is coupled to the (e.g., structure 110) and imaging system 102 rotates relative to the structure (e.g., structure 110) while emitting the X-rays (e.g., first pencil beam 218 and second pencil beam 220) and detecting the backscattered X-rays (e.g., first backscattered X-rays 606 and second backscattered X-rays 608).

In some implementations, imaging system 102 generates parallel slices of image data (e.g., image data 520) corresponding to a plurality of depths 224 within structure 110. In some implementations, imaging system 102 combines image data from two angles (e.g., angles α and β) along a plane 1002 that is perpendicular to the structure (e.g., structure 110).

In some implementations, imaging system 102 includes a platform (e.g., platform 108) that includes a first stage (e.g., first stage 812) that is adapted to translate along a first axis (e.g., first axis 832), a second stage (e.g., second stage 814) that is coupled to the first stage (e.g., first stage 812) and is adapted to translate along a second axis (e.g., second axis 834) that is perpendicular to the first axis (e.g., first axis 832), and at least one rail (e.g., first rail 816) that is coupled to at least the first stage (e.g., first stage 812) and is adapted to mount to the structure (e.g., structure 110).

In some implementations, imaging system 102 generates first image data 520 for a plurality of first points (e.g., line 216) at a first depth (e.g., depth 224), then generates second image data for a plurality of second points at a second depth in the structure (e.g., structure 110). In some implementations, imaging system 102 generates first image data 520 at a first plurality of depths 224 along a first plane 216 within the structure (e.g., structure 110), then generates second image data at a second plurality of depths along a second plane that is adjacent to the first plane.

A technical effect of systems and methods described herein includes at least one of: (a) emitting X-rays from at least one X-ray source through at least one rotating collimator towards one side of a structure; (b) detecting backscattered X-rays from the one side of the structure, using an X-ray detector, at a plurality of depths within the structure; and (c) generating three dimensional image data of the structure based on the detected backscattered X-rays.

As compared to known methods and systems for performing imaging of a structure, the systems and methods described herein enable generating three dimensional images of internal features of a structure while only accessing a single side of the structure. Accordingly, users of the systems and methods described herein may view and evaluate three dimensional image data of features within a structure without the need to disassemble the structure or have access to more than one side of the structure. More specifically, the systems and methods described herein solve an important problem pertaining to non-destructive evaluation and quantification of wrinkles in composite structures. Namely, the system and methods described herein provide the ability to see under a wrinkle in a composite structure to determine its depth, thickness, and magnitude.

The description of the different advantageous implementations has been presented for purposes of illustration and description, and is not intended to be exhaustive or limited to the implementations in the form disclosed. Many modifications and variations will be apparent to those of ordinary skill in the art. Further, different advantageous implementations may provide different advantages as compared to other advantageous implementations. The implementation or implementations selected are chosen and described in order to best explain the principles of the implementations, the practical application, and to enable others of ordinary skill in the art to understand the disclosure for various implementations with various modifications as are suited to the particular use contemplated. This written description uses examples to disclose various implementations, which include the best mode, to enable any person skilled in the art to practice those implementations, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An imaging system for generating three dimensional image data using X-ray backscattering from a first side of a structure, said imaging system comprising:
    a first X-ray source and a second X-ray source;
    a first rotating collimator coupled to said first X-ray source and to a second rotating collimator coupled to said second X-ray source;
    a first shutter coupled to said first rotating collimator and a second shutter coupled to said second rotating collimator;
    an X-ray detector; and
    a controller coupled to said first and second X-ray sources, said first and second rotating collimators, and said X-ray detector, said controller is configured to:
    emit a first X-ray beam through said first rotating collimator at a first point in the structure through the first side of the structure while the second shutter is closed;
    detect backscattered X-rays from the first X-ray beam from the first side of the structure;
    emit a second X-ray beam through said second rotating collimator at the first point through the first side of the structure while said first shutter is closed; and
    detect backscattered X-rays from the second X-ray beam from the first side of the structure; and
    generate three dimensional image data of the structure based on the detected backscattered X-rays from the first side of the structure.

2. The imaging system of claim 1, further configured to:
    emit the first X-ray beam at a first point in the structure through the first side of the structure from a first angle;
    detect first backscattered X-rays from the first X-ray beam from the first side of the structure;
    generate first image data from the first backscattered X-rays;
    emit the second X-ray beam at the first point in the structure through the first side of the structure from a second angle;
    detect second backscattered X-rays from the second X-ray beam from the first side of the structure;
    generate second image data from the second backscattered X-rays; and
    combine the first image data with the second image data.

3. The imaging system of claim 1, further comprising a platform that is coupled to the structure, wherein said imaging system is further configured to rotate relative to the first side of the structure while emitting the X-rays and detecting the backscattered X-rays.

4. The imaging system of claim 1, further configured to generate parallel slices of image data corresponding to a plurality of depths within the structure.

5. The imaging system of claim 1, further configured to combine image data from two angles along a plane that is perpendicular to the structure.

6. The imaging system of claim 1, further configured to generate first image data for a plurality of first points at a first depth, then generate second image data for a plurality of second points at a second depth in the structure.

7. The imaging system of claim 1, further configured to generate first image data at a first plurality of depths along a first plane within the structure, then generate second image data at a second plurality of depths along a second plane that is adjacent to the first plane.

8. A method for generating three dimensional image data using X-ray backscattering from a first side of a structure, said method comprising:
    emitting a first X-ray beam through a first rotating collimator at a first point in the structure through the first side of the structure while a first shutter of the first rotating collimator is open and a second shutter of a second rotating collimator is closed;
    detecting backscattered X-rays from the first X-ray beam from the first side of the structure;
    emitting a second X-ray beam through the second rotating collimator at the first point through the first side of the structure while the second shutter of the second rotating collimator is open and the first shutter of the first rotating collimator is closed; and
    detecting backscattered X-rays from the second X-ray beam from the first side of the structure; and
    generating three dimensional image data of the structure based on the detected backscattered X-rays from the first side of the structure.

9. The method of claim 8, further comprising:
    emitting the first X-ray beam at a first point in the structure through the first side of the structure from a first angle;
    detecting first backscattered X-rays from the first X-ray beam from the first side of the structure;
    generating first image data from the first backscattered X-rays;
    emitting the second X-ray beam at the first point in the structure through the first side of the structure from a second angle;
    detecting second backscattered X-rays from the second X-ray beam from the first side of the structure;
    generating second image data from the second backscattered X-rays; and
    combining the first image data with the second image data.

10. The method of claim 8, wherein the first and second rotating collimators, the first and second X-ray sources, and the X-ray detector are included in an imaging system, said method further comprising rotating the imaging system relative to the first side of the structure while emitting the X-rays and detecting the backscattered X-rays.

11. The method of claim 8, further comprising generating parallel slices of image data corresponding to a plurality of depths within the structure.

12. The method of claim 8, further comprising combining image data from two angles along a plane that is perpendicular to the structure.

13. The method of claim 8, further comprising:
    generating first image data for a plurality of first points at a first depth; and
    subsequently generating second image data for a plurality of second points at a second depth in the structure.

14. The method of claim 8, further comprising:
    generating first image data at a first plurality of depths along a first plane defined within the structure; and
    subsequently generating second image data at a second plurality of depths along a second plane defined within the structure that is adjacent to the first plane.

* * * * *